(12) United States Patent
Mbalaviele (10) Patent No.: US 6,239,157 B1
(45) Date of Patent: May 29, 2001

(54) INHIBITION OF OSTEOCLASTOGENESIS

(75) Inventor: Gabriel Mbalaviele, Columbia, MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/393,434

(22) Filed: Sep. 10, 1999

(51) Int. Cl.[7] .................................................. A01N 43/78
(52) U.S. Cl. ........................ 514/369; 514/415; 514/573
(58) Field of Search ................................. 514/369, 415, 514/573

(56) References Cited

PUBLICATIONS

Kawaguchi, et al., *Clin. Orthopaedics,* vol. 313, pp. 36–46 (Apr. 1995).

Aota, et al., *Calcif. Tissue Int.,* vol. 59, No. 5, pp. 385–391 (Nov. 1996).

Lane, et al., *J. Rheumatol.,* vol. 24, No. 6, pp. 1132–1136 (Jun. 1997).

Ricote, et al., *Nature,* vol. 391, pp. 79–82 (Jan. 1, 1998).

Jiang, et al., *Nature,* vol. 391, pp. 82–86 (Jan. 1, 1998).

Bornefalk, et al., *Eur. J. Pharmacol.,* vol. 345, No. 3, pp. 333–338 (Mar. 1998).

Taki, et al., *Clin. Exp. Immunol.,* vol. 112, No. 1, pp. 133–138 (Apr. 1998).

Spiegelman, *Cell,* vol. 93, pp. 153–155 (Apr. 17, 1998).

Lader, et al., *Endocrinology.* vol. 139, No. 7, pp. 3157–3164 (Jul. 1998).

*Primary Examiner*—Theodore J. Criares
(74) *Attorney, Agent, or Firm*—Elliot M. Olstein; Raymond J. Lillie (57) ABSTRACT

A method for inhibiting the differentiation of CD34+ cells into osteoclasts by treating the cells with a peroxisome proliferator-activated receptor-γ agonist.

5 Claims, 8 Drawing Sheets

INHIBITION OF OSTEOCLASTOGENESIS

The present invention relates to inhibiting osteoclast production and more particularly to a process and composition for regulating the differentiation of human hematopoietic stem cells into osteoclasts. The invention further relates to reducing bone resorption.

BACKGROUND OF THE INVENTION

Osteoclasts arise from hematopoietic stem cells and are the primary cells responsible for physiological and pathological bone resorption. Changes in the levels of cytokines and growth factors in bone microenvironment cause abnormal bone resorption by the osteoclasts (for a review see Mundy, et al., 1997). Accordingly, forced expression of IL-4 (Lewis, et al., 1993), and G-CSF (Takahashi, et al., 1996) in mice induced osteopenia, while mice overexpressing soluble TNF-α receptor (Ammann, et al., 1997) or depleted of the IL-6 gene (Poli, et al., 1994) are protected against bone loss caused by estrogen deficiency. Recent studies have demonstrated that OPGL is an essential and sufficient regulator of osteoclast differentiation, activity and survival (Kong, et al., 1999).

SUMMARY OF THE INVENTION

It has been found that the differentiation of CD34+ cells into osteoclasts is inhibited by treatment of the hematopoietic stem cells with peroxisome proliferator-activated receptor-γ (PPAR-γ) agonists. The CD34+ cells may be hematopoietic stem cells (HSCs).

Accordingly, the present invention provides a method for inhibiting the differentiation of HSCs into osteoclasts by treating the HSCs with PPAR-γ agonists in an amount sufficient to inhibit differentiation into osteoclasts.

In accordance with an embodiment of the present invention, the production of osteoclasts is reduced, in vivo, by administering an amount of a PPAR-γ agonist in an amount that is effective for reducing such production. The present invention also is applicable to reducing such production, in vitro, by the use of such an agonist.

In accordance with yet another object of the present invention, there is provided a process for treating osteoporosis in an animal, in particular a human, by administering an amount of a PPAR-γ agonist effective for such treatment.

In a preferred embodiment the PPAR-γ agonist is the PPAR-γ ligand 15-deoxy-$\Delta^{12,14}$-prostaglandin-J2 (15d-PG-J2).

In another embodiment, bone resorption is inhibited by treatment with a PPAR-γ agonist. More particularly, the bone resorption caused by osteoclasts is inhibited by use of such an agonist.

BRIEF DESCRIPTION OF THE DRAWINGS

FIG. 1.

A—Expression of OPG and OPGL mRNA during osteogenic differentiation of hMSCs. cDNAs were reverse-transcribed using total RNA which were isolated from hMSCs or hMSCs treated with osteogenic supplement (OS) for 4 (lane 3), 8 (lane 5) or 15 (lane 7) days. Control hMSCs were maintained in culture for the same lengths of time. PCR was carried out using the primers specific to OPGL (Top panel) or OPG (middle panel). The data show that OS treatment decreased OPGL mRNA levels while increasing OPG MRNA levels. Bottom panel, control amplification of β2-microglobulin mRNA.

B—Competitive RT-PCR for quantification of OPG and OPGL mRNA levels during osteogenic differentiation of hMSCs. cDNAs were reverse-transcribed using total RNA isolated from hMSCs maintained in cultures for 15 days (lanes 1–8) or hMSCs treated with OS for 15 days (lanes 1'–8'). The data showed that in osteogenic hMSCs OPG mRNA levels were ~100 times higher than OPGL mRNA and that OPGL mRNA levels in untreated hMSCs were ~10 times higher than OPG mRNA.

FIG. 3.

A—RT-PCR analysis of PPAR-γ mRNA expression. cDNAs were reverse-transcribed using total RNA isolated from five different donors of hMSCs (lanes 1–5) or same hMSCs treated with MDII (lanes 1'–5') or two different donors of CD34+ HSCs (lanes 6 and 7). CD34+ HSCs or hMSCs treated with MDII expressed PPAR-γ mRNA which was undetectable in hMSCs. Bottom, control amplification of β2-microglobulin mRNA.

B—Northern analysis of PPAR-γ mRNA expression. Total RNA was isolated from untreated hMSCs (lane 1) or hMSCs treated with MDII for 1 (lane 2), 3 (lane 3) or 5 days (lane 4).

FIG. 4.

A—Photomicrographs of Ocl formed in the absence or presence of PPAR-γ 15d-PG-J2. CD34+ HSCs and hMSCs were treated with sOPGL and M-CSF in the absence (A) or presence (B) of 15d-PG-J2. Arrows and star sign indicate Ocls and hMSCs, respectively. Note the complete inhibition of Ocl formation in 15d-PG-J2-treated cultures despite the presence of Ocl precursors (arrowheads). Star sign indicates hMSCs.

C—Quantitation of the effects of PPAR-γ agonists on Ocl formation. CD34+ HSCs and hMSC cocultures were treated with sOPGL+M-CSF in the absence or presence of 15d-PG-J2, ciglitazone, or PG-J2. *p<0.01 versus untreated hMSC and CD34+ HSC cocultures.

Table I: Ocls were purified from cocultures as described in Materials and Methods then plated onto hMSCs which had been seeded onto elephant tusk slices. Cocultures were treated with 40 ng/ml sOPGL and 25 ng/ml M-CSF with or without 10 μM 15d-PG-J2 for 24 h. Note that treatment with 15d-PG-J2 for 24 h did not affect the numbers of Ocls but inhibited bone resorption.

BRIEF DESCRIPTION OF THE INVENTION

Applicants have found that the induction of the differentiation of the CD34+ hematopoietic stem cells (HSCs) into osteoclasts is inhibited by treatment with PPAR-γ agonists, such as ciglitazone, pioglitazone, troglitazone, and indomethacin. In a preferred embodiment the PPAR-γ agonist is the PPAR-γ ligand 15-deoxy-$\Delta^{12,14}$-prostaglandin-J2 (15d-PG-J2).

The peroxisome proliferator-activated receptor-γ (PPAR-γ) is a member of the nuclear receptor superfamily of transcription factors, expressed in adipose tissue, adrenal gland, spleen, endothelium and hematopoietic tissue (Kliewer, et al., 1995; Ricote, et al., 1998; Jiang, et al., 1998; Xin, et al., 1999). Treatment of HL60 monocytic leukemia cells and monocytes with PPAR-γ agonists results in the formation of foam cells (Tontonoz, et al., 1998; Nagy, et al., 1998). In contrast, treatment of activated monocytes/ macrophages with PPAR-γ agonists reduces the expression of inflammatory molecules including inducible nitric oxide synthase, gelatinase B, scavenger receptor A, interleukin (IL)-6, IL-1β, and tumor necrosis factor α (TNF-α) in response to phorbol ester stimulation (Ricote, et al., 1998; Jiang, et al., 1998). These studies show that PPAR-γ regulates several functions of lineage-committed hematopoietic cells. PPAR-γ must heterodimerize with the retinoic X receptor to serve as a transcription regulator of target genes. It cooperates with the members of the C/EBP family to initiate adipocyte differentiation (for a review, see Lane, 1997) and inhibits gene expression in monocytes/ macrophages in part by antagonizing the activity of other transcription factors including NF-κB, AP-1, and STAT (Ricote, et al., 1998). Of interest, the NF-κB family of transcriptional activators regulates genes controlling the fate of a variety of cells including the osteoclast lineage. It has been shown that mice deleted of the p50/p52 heterodimer of the NF-κB/Rel family exhibited osteoporosis due to a deficiency in osteoclast differentiation (Franzoso, et al., 1997; Iotsova, et al., 1997).

Applicants have found that hMSCs express osteoprotegerin ligand (OPGL) which is an essential Ocl differentiation factor, osteoprotegerin (OPG), and macrophage-colony stimulating factor (M-CSF). Competitive RT-PCR analysis was performed on hMSC RNA to show that basal levels of OPGL mRNA in hMSCs were $\geq 10$ times greater than those of OPG mRNA, consistent with the ability of hMSCs to support Ocl formation. Addition of soluble(s)-OPGL and M-CSF to the cocultures stimulated Ocl formation up to 10-fold compared to untreated cocultures.

Having found that CD34$^+$ HSCs express PPAR-γ, the Applicants next examined the effects of PPAR-γ agonists on Ocl formation and found that 15-deoxy-$\Delta^{12,14}$-prostaglandin-J2 (15d-PG-J2) inhibited Ocl formation in the cocultures without evidence of cytotoxicity. Remarkably, 15d-PG-J2 completely blocked sOPGL and M-CSF-induced Ocl formation. 15d-PG-J2 also inhibited bone resorption by isolated osteoclasts.

The Applicants showed that sOPGL activated NF-κB pathway within the Ocl precursors, an effect which was inhibited by 15d-PG-J2. These data show that hematopoietic stem cells express PPAR-γ. They also establish a link between PPAR-γ and sOPGL and support a role for PPAR-γ pathway in the modulation of osteoclastogenesis.

The agonists may be employed in a composition with a pharmaceutically acceptable carrier. Such compositions comprise a therapeutically effective amount of the polypeptide, and a pharmaceutically acceptable carrier or excipient.

Carriers which may be employed include, but are not limited to, saline, buffered saline, dextrose, water, glycerol, ethanol, and combinations thereof. The formulation should suit the mode of administration.

The pharmaceutical compositions may be administered in a convenient manner such as by the topical, intravenous, intraperitoneal, intramuscular, intratumor, subcutaneous, intranasal, or intradermal routes. The pharmaceutical compositions are administered in an amount which is effective for treating the specific indication. In general, the agonists are administered in an amount of at least about 100 μg/kg body weight, and in most cases it is administered in an amount not in excess of about 300 μg/kg body weight per day, taking into account the routes of administration, symptoms, etc.

EXAMPLE

Materials and Methods

Reagents

Ciglitazone, 15d-PG-J2 and PG-J2 were purchased from Biomol Research Laboratory (Plymouth Meeting, Pa.). Echistatin, dexamethasone, indomethacin, insulin, and PG-E2 were from Sigma (St. Louis, Mo.). Collagenase was from Wako Chemicals USA (Richmond, Va.). Dispase was obtained from Boehringer Mannheim (Indianapolis, Ind.). M-CSF and sOPGL were purchased from PeproTech, Inc. (Rocky Hill, N.J.)

Isolation and Adipogenic Differentiation of hMSCs

Human bone marrow aspirates were purchased from Poietic Technologies, Inc. (Gaithersburg, Md.). hMSCs were isolated from fresh bone marrow aspirates and culture-expanded as previously described (Jaiswal, et al., 1997). hMSC culture medium consisted of Dulbecco's Modified Eagles Medium-Low Glucose (DMEM-LG) (Hyclone, Salt Lake City, Utah) supplemented with 10% fetal bovine serum (FBS) (Biocell Laboratories, Rancho Dominquez, Calif.) and 1% antibiotic-antimycotic solution (Life Technologies, Grand Island, N.Y.).

Adipogenic differentiation of hMSCs was induced as previously described (Jaiswal, et al., 1997). Briefly, hMSCs were plated at a density of $2 \times 10^4$ cells per cm$^2$ and cultured in hMSC medium until they reach confluence. Cultures then were maintained in adipocyte medium (MDII) containing DMEM-high glucose (DMEM-HG), 10% FBS and 10 μg/ml insulin, 1 μM dexamethasone, 0.1 mM indomethacin and 0.5 mM isobutyl methyl xanthine. After 72 hrs. the cultures were incubated for 24 hrs. with adipocyte maintenance medium (AM) containing 10% FBS and 10 μg/ml insulin. This sequence is repeated three times after which the cultures were grown in AM for 1 week. Medium was changed every 3–4 days. Half cultures were then fixed and stained with Oil-Red O to visualize adipocytes, and the remaining cultures were used for RNA isolation.

Cell Cultures

CD34$^+$ HSCs were immunoaffinity purified (purity>95%) from healthy human bone marrow by Poietic Technologies, Inc. (Gaithersburg, Md.). Aliquots ($5 \times 10^4$/cm$^2$) of cryopreserved CD34$^+$ HSCs were added to monolayers of hMSCs. The cocultures were maintained in DMEM-LG supplemented with 10% fetal bovine serum in the presence or absence of 40 ng/ml sOPGL and/or 25 ng/ml M-CSF for 3 weeks at 37° C. in 95% air, 5% CO$_2$. Every 3 days, half of the culture medium was removed gently to minimize loss of non-adherent cells and replaced with an equal volume of fresh medium.

Bone marrow macrophages (BMMs) were isolated from whole bone marrow of 4–6-week-old mice and incubated in tissue culture plates, at 37° C. in 5% CO$_2$, in the presence of M-CSF (1,000 units/ml). After 24 hrs. in culture, the non-adherent cells were collected and layered on a Ficoll-Hypaque gradient and cells at the gradient interface were collected and plated in α-minimal essential medium, supplemented with 10% heat-inactivated fetal bovine serum, at 37° C. in 5% CO$_2$ in the presence of M-CSF (1,000 units/ml).

Bone Resorption

Bone resorption by the Ocls in vitro was assessed using smoothened elephant tusk slices (4×4×0.1 mm) as described (Mbalaviele, et al., *Endocrinology*, Vol. 140, pgs. 3736–3743 (1999)). Ocls and Ocl precursor cells were harvested from hMSCs and CD34+ HSC co-cultures treated with 40 ng/ml sOPGL and 25 ng/ml M-CSF for 1 week as described (Wesolowski, et al., (1995)). Briefly, cocultures were washed twice with PBS, treated twice with collagenase and dispase (1 mg/ml, each) diluted in PBS for 15 min. at 37° C. The supeCatants containing hMSCs were discarded. Adherent cells consisting of Ocls and Ocl precursor cells were washed vigorously 3 times with PBS, detached from the dishes following treatment twice with 30 nM echistatin diluted in DMEM-LG containing 1% BSA for 20 min. each at 37° C., then with 0.05% trypsin for 20 min. at 37° C. The detached cells were washed twice with hMSC medium by centrifugation, and plated onto sterile tusk slices on which confluent hMSCs were pre-seeded. Cocultures were maintained for 24 hrs. in the absence or presence of sOPGL, M-CSF and 15d-PG-J2. At the end of the culture period, cells were stained for TRAP activity to visualize Ocls, subsequently incubated with a 0.1 M NaOH solution followed by ultrasonication for 2 min. Slices were placed in a 1% aqueous toluidine blue solution containing 1% sodium borate for 5 min. Photomicrography of resorption pits was taken using light microscopy.

Tartrate-resistant Acid Phosphatase (TRAP) Staining

At the end of the culture period, the medium was removed and the cells were fixed for 30 sec. by addition of a 60% acetone solution prepared in citrate buffer (pH5.4). The fixed cells were washed twice with distilled water and air-dried. Tartrate-resistant acid phosphatase-positive (TRAP+) cells were detected using a TRAP staining kit (Sigma, St. Louis, Mo.). TRAP+ multinucleated cells (three or more nuclei, TRAP+MNCs) were counted manually using a light microscope (Mbalaviele, et al., 1998).

RNA Isolation for RT-PCR Analysis

Total RNA was extracted from cell cultures using the High Pure RNA Isolation kit (Boehringer Mannheim, Indianapolis, Ind.). RT-PCR was performed for up to 40 cycles on single-stranded cDNA prepared from total RNA (1 μg) using a GeneAmp RT-PCR kit (Perkin Elmer, Foster City, Calif.). The upstream primer (up) and downstream primer (dp) were designed as follows: OPG: 5'-ACCACTACTACACAGACAGC-3' and 5'-AGTCATGTTGGAGATCTTGG-3'. OPGL: 5'-TTCTATTTCAGAGCGCAGAT-3' and 5'-AGTCATGTTGGAGATCTTGG-3'. PPAR-γ: 5'-ATGGGTGAAACTCTGGGAGA-3' and 5'-GTACTCTTGAAGTTTCAGGTC-3'. Competitive RT-PCR was performed in the presence of increasing concentrations (0.00001–10 fmoles) of a homologous competitor DNA. The upstream primer 5'-TTCTATTTCAGA GCGCAGATACCACTACTACACAGACAGC-3' and the downstream primer 5'-AGGAGACCAAAGACA CTGCAAGTCATGTTGGAGATCTTGG-3' annealed to both OPG and OPGL cDNA as well as the competitor DNA fragment.

Northern Blotting

Total RNA was isolated from hMSCs or hMSCs treated with MDII for 1, 3, or 5 days using Tri-Reagent (Molecular Research Center Inc., Cincinnati Ohio) according to the manufacturer's protocol. 20 ug samples were electrophoresed through a 1% agarose formaldehyde gel and transferred by capillary blotting onto a nitrocellulose membrane. After prehybridization the blot was hybridized with the mouse PPAR-γ2 cDNA fragment, a gift from Dr. Jeffrey Kimble (Oklahoma City, Okla.). The fragment was double labeled with [$^{32}$P]dCTP using the random primers DNA labeling kit (Gibco-BRL). Signals were detected using Storm Phosphoimager screens (Molecular Dynamics, Sunnyvale Calif.).

Electrophoretic Mobility Shift Assay

Nuclear fractions were prepared as described previously (Abu-Amer, 1998). In brief, untreated or sOPGL-stimulated monolayers of BMMs grown in 100-mm$^2$ tissue culture dish were washed twice with ice-cold PBS, treated with 5 mM EDTA and 5 mM EGTA in PBS, then resuspended in hypotonic lysis buffer A (10 mM HEPES, pH 7.8, 1.5 mM MgCl, 0.5 mM dithiothreitol, 0.5 mM AEBSF, 5 μg/ml leupeptin) and incubated on ice for 15 min., and Nonidet P-40 was added to a final concentration of 0.64%. Nuclei were pelleted and the cytosolic fraction was removed, resuspended in nuclear extraction buffer B (20 mM HEPES, pH 7.8, 420 mM NaCl, 1.2 mM MgCl, 0.2 mM EDTA, 25% glycerol, 0.5 mM dithiothreitol, 0.5 mM AEBSF, 5 μg/ml pepstatin A, 5 μg/ml leupeptin) and rotated for 30 min. at 4° C. The samples were centrifuged and the supernatant were transferred to fresh tubes and protein content was measured using standard BCA kit (Pierce, Rockford, Ill.). Nuclear extracts (10 μg) were incubated with an end-labeled double-stranded oligonucleotide probe containing the sequence 5'-AAACAGGGGGCTTTCCCTCCTC-3' derived from the B3 site of the TNF promoter. The reaction was performed in a total of 20 μl of binding buffer (20 mM HEPES, pH 7.8, 100 mM NaCl, 0.5 mM dithiothreitol, 1 μg of poly(dI-dC), and 10% glycerol) for 15–20 min. at room temperature. For supershift assay, the nuclear extract was incubated with specific antibodies for 30 min. before addition of the labeled probe. After incubation with the labeled probe for an additional 30 min., samples were fractionated on a 4% polyacrylamide gel and visualized by exposing dried gel to film.

Statistical Analysis

All data were analyzed by a paired t test. Samples were run in triplicates and data represent the mean±SE. Each experiment was repeated at least twice.

RESULTS

Expression of OPG and OPGL by hMSCs

Figure 1A:
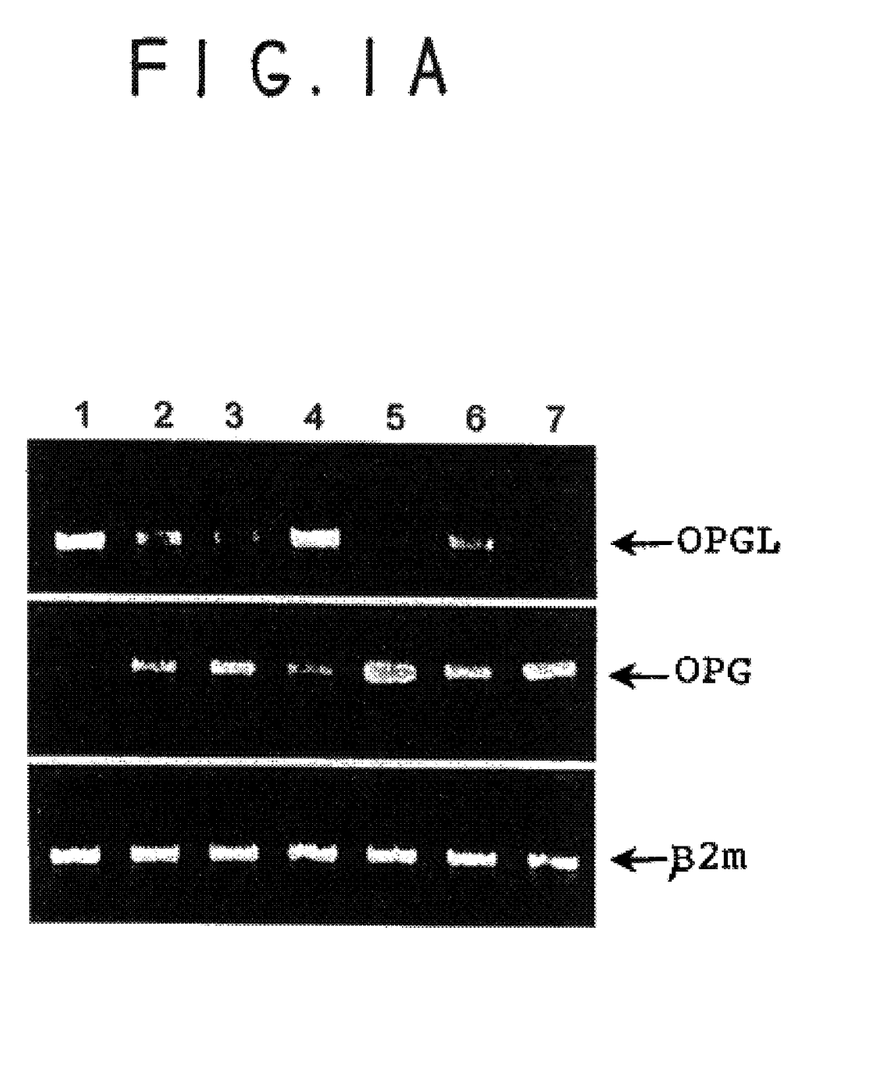
Figure 1B:
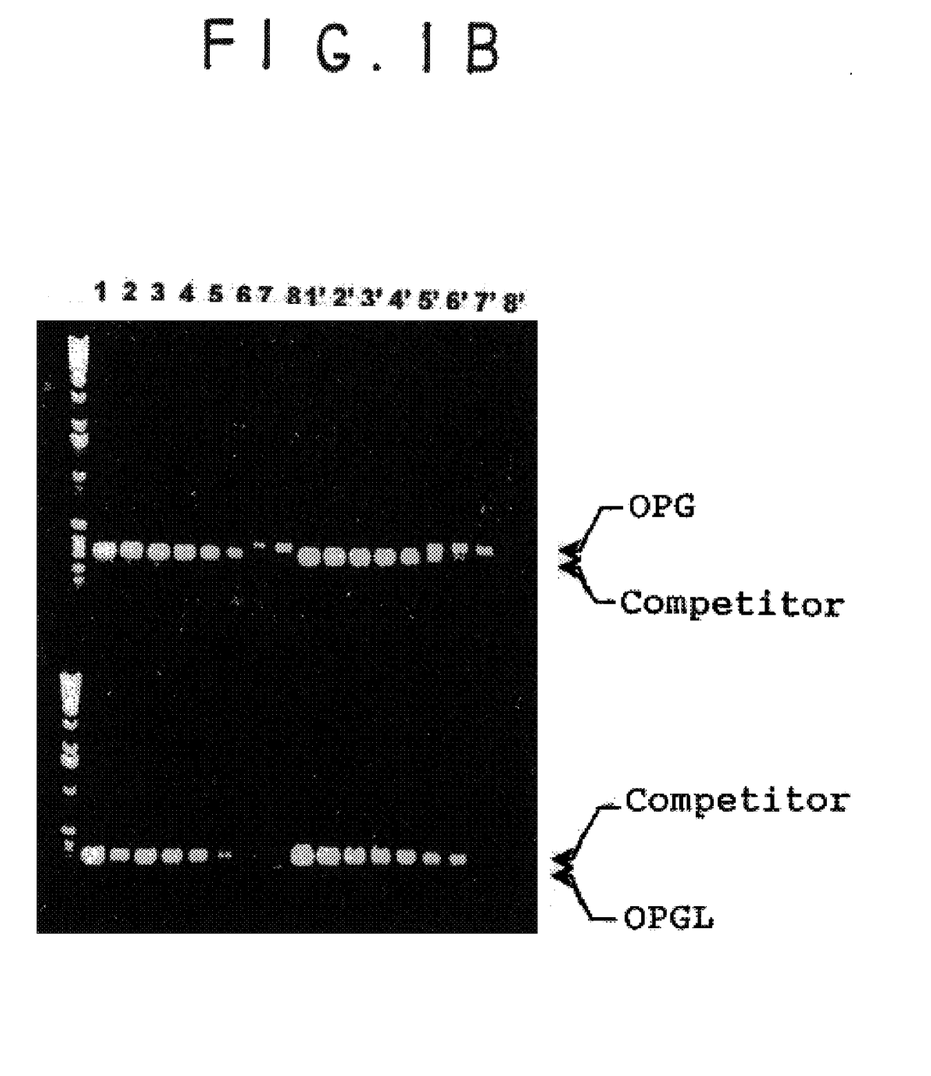

We have shown recently that hMSCs promote Ocls formation from CD34+ HSCs in vitro (Mbalaviele, et al., in press). This led us to examine if osteoprotegerin (OPG) and its ligand OPGL are expressed by hMSCs. OPGL stimulates Ocl development, on the other hand OPG blocks OPGL effects (Lacey, et al., 1998). Using RT-PCR techniques we found that hMSCs expressed both OPG and OPGL mRNA (FIG. 1). We also have shown that treatment of hMSCs with substances which promote osteogenic differentiation of hMSCs inhibit the ability of these cells to support Ocl formation (Mbalaviele, et al., in press). In this study we found that osteogenic differentiation of hMSCs is associated with concomitant decline in OPGL mRNA levels and increase in OPG mRNA levels (FIG. 1). Quantitative competitive RT-PCR was used to demonstrate that levels of OPGL MRNA in untreated hMSCs were ~10 times higher than levels of OPG mRNA. In contrast, OPG mRNA levels in osteogenic hMSCs were ~100 times higher than OPGL MRNA (FIG. 1B). The data indicate that differentiation of hMSCs into osteogenic hMSCs is associated with a decrease in OPGL/OPG ratio.

Role of OPGL in hMSC-based Osteoclastogenesis

Figure 2:
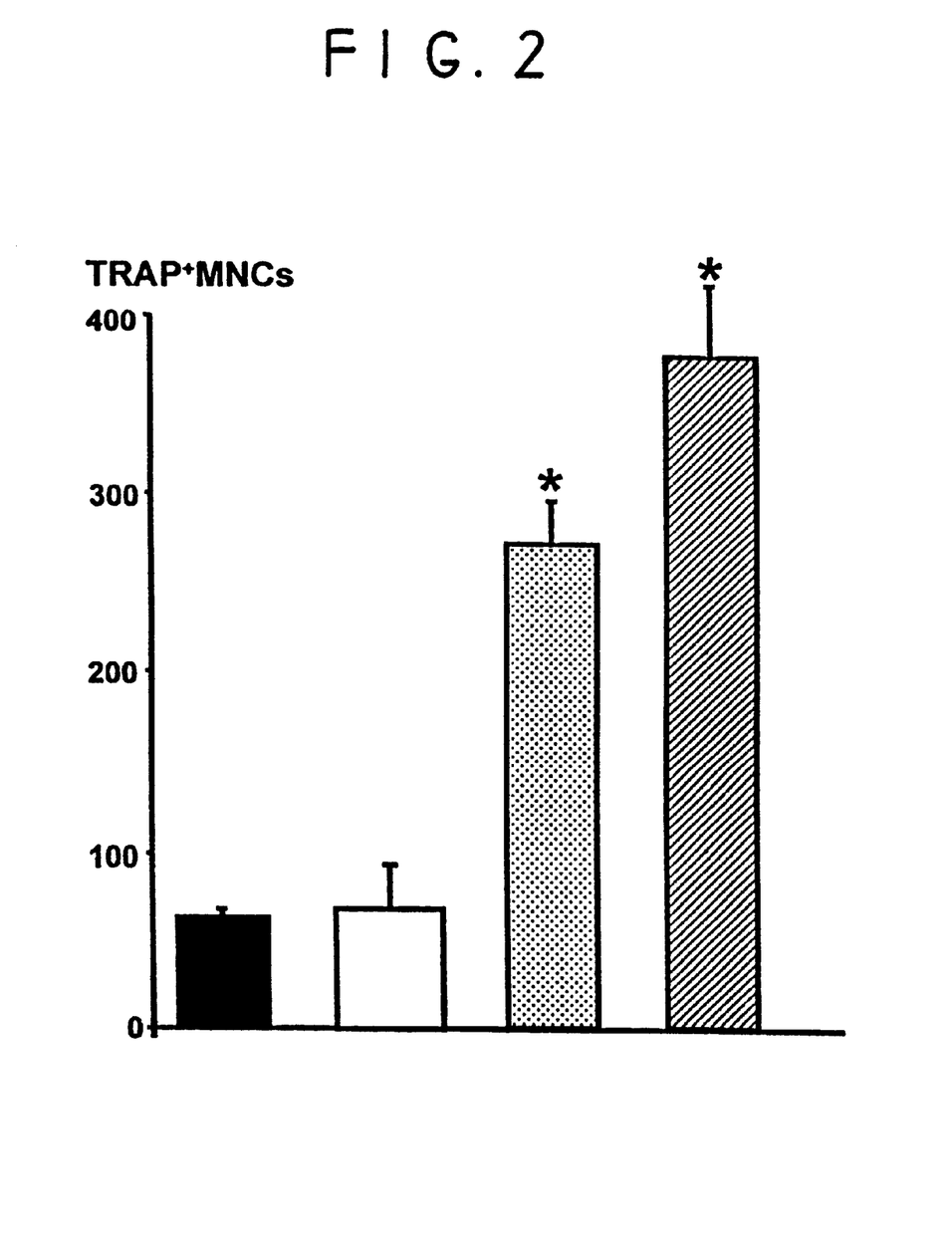
FIG. 2. Role of OPGL in hMSC-based osteoclastogenesis. CD34+ HSCs and hMSCs were cocultured in the absence (■) or presence of 20 ng/ml M-CSF (□), 30 ng/ml sOPGL (▨) or sOPGL and M-CSF (●) for 12 days. *p<0.01 versus untreated hMSCs and CD34+ cell cocultures.

To examine the role of OPGL in hMSC-based osteoclastogenesis, CD34+ HSCs and hMSC cocultures were with soluble (s)OPGL. After 1 week, cocultures treated with sOPGL had Ocl formation ~3 times more than untreated cocultures. Addition of M-CSF alone had no effect on Ocl formation in the cocultures, but the combination of both sOPGL and M-CSF stimulated Ocl formation by ~10-fold compared to untreated cocultures (FIG. 2). sOPGL and M-CSF induced Ocl formation in the absence of hMSCs only after 3 weeks of cultures, and the number of Ocls was lower than in cultures with sOPGL and M-CSF-treated hMSCs (data not shown).

PPAR-γ expression

Figure 3A:
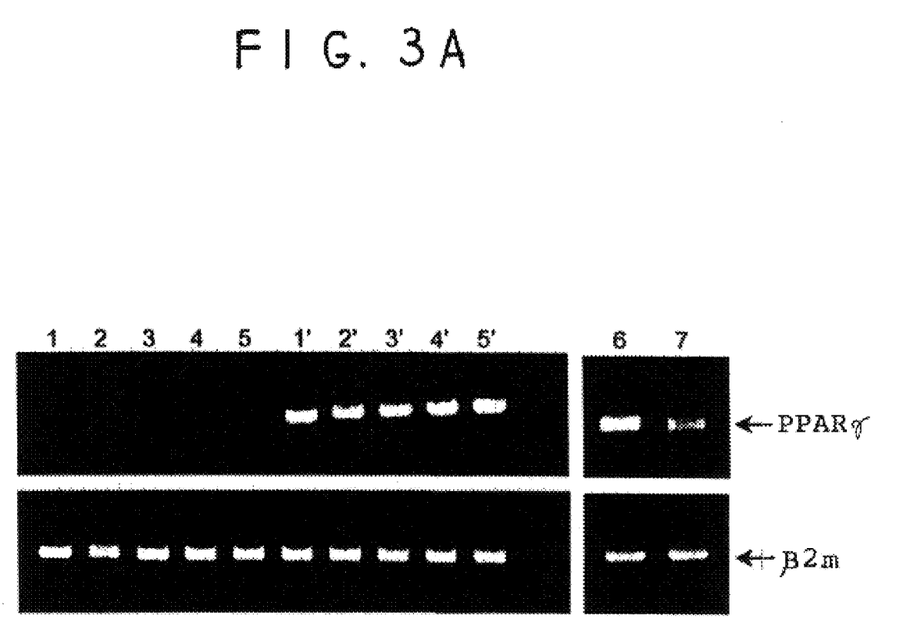
Figure 3B:
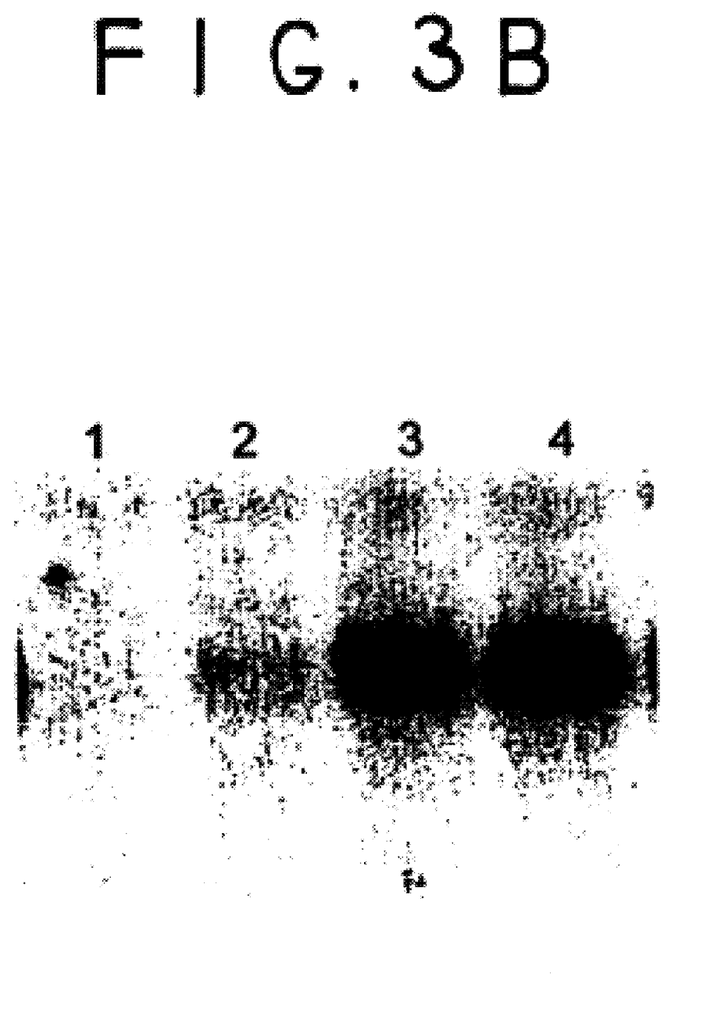

Evidence that PPAR-γ is expressed by the cells of both the hematopoietic and mesenchymal lineages led us to determine PPAR-γ expression in hMSCs and CD34+ HSCs. We used RT-PCR and Northern techniques to demonstrate that CD34+ HSCs and hMSCs which have been induced to differentiate into adipocytes ($\geq$90% of the cells in culture) upon treatment with MDII expressed PPAR-γ mRNA (FIG. 3). The DNA amplicons generated by PCR were of expected size, which after sequencing exhibited 100% identity to PPAR-γ2. In contrast, PPAR-γ mRNA was not detected in untreated hMSCs.

Effects of PPAR-γ agonists on Ocl formation

Figure 4A:
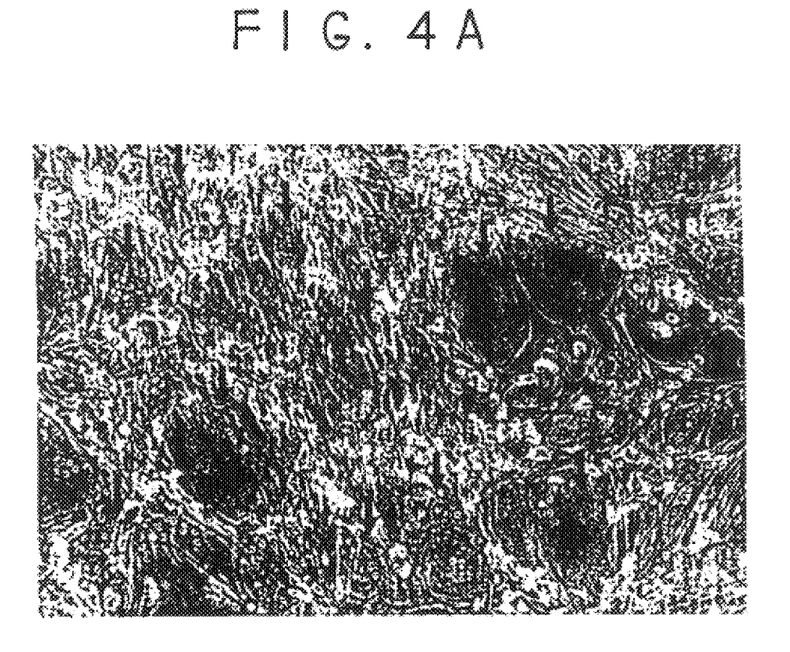
Figure 4B:
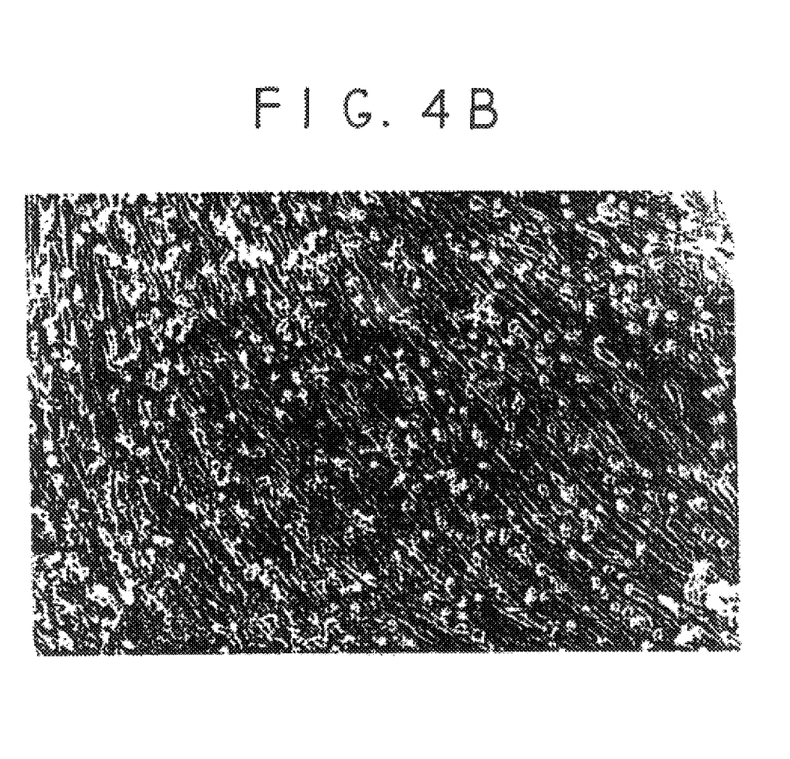
Figure 4C:
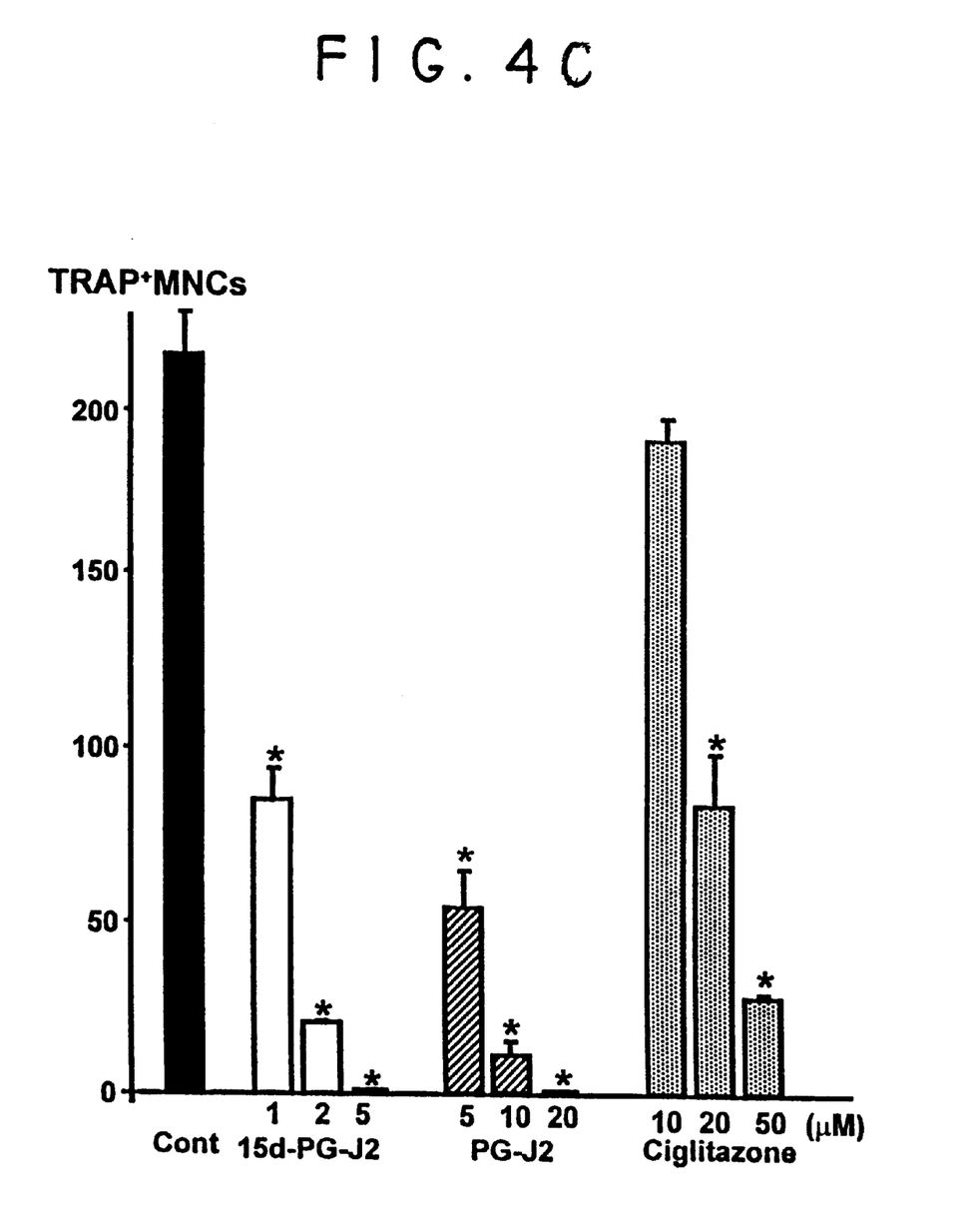

The expression of PPAR-γ by CD34+ HSCs led us to examinee the effects of PPAR-γ agonists on the ability of sOPGL to induce Ocl formation in the cocultures. Addition of 15d-PG-J2 at low concentrations (0–5 $\mu$M) as compared to other systems dose-dependently blocked sOPGL and M-CSF-induced Ocl formation in the absence or presence of hMSCs without any cytotoxic effect on either hMSCs or hematopoietic cells (FIG. 4B). Treatment with 15d-PG-J2 did not induce adipocyte differentiation from hMSCs. 15d-PG-J2 inhibited the differentiation of TRAP+ mononucleated cells (Ocl precursors), suggesting that it interfered with early events involving Ocl differentiation. Quantitative data showed 15d-PG-J2>PG-J2>ciglitazone in inhibiting Ocl formation. The addition of PG-E2 actually stimulated Ocl formation by ~2-fold (data not shown). The finding that 15d-PG-J2 inhibited Ocl formation induced by the combinations of IL-1, IL-3, and GM-CSF (data not shown) suggests that PPAR-γ agonists broadly regulate cytokine-induced both human and mouse osteoclastogenesis.

Effects of PPAR-γ Agonists on Ocl Activity

To determine if 15d-PG-J2 effects the ability of pre-formed Ocls to resorb bone, Ocls were purified from CD34+ HSCs and hMSCs cocultures which were treated for 1 week with 40 ng/ml sOPGL and 25 ng/ml M-CSF. The purified Ocls then were plated onto elephant tusk slices with or without hMSCs. Treatment with 15d-PG-J2 during the 24 hrs. did not affect the numbers of Ocls (108±18 versus 107±6, in the absence or presence of 15d-PG-J2, respectively) suggesting that their attachment to bone matrix was not affected (Table I). However, we noted that the Ocls in 15d-PG-J2-treated cocultures were rounded and exhibited high TRAP staining intensity, certainly due to cell retraction. In contrast, we found that the treatment of cultures with 15d-PG-J2 decreased bone resorption stimulated by sOPGL and M-CSF (Table I). In the absence of hMSCs, there was a marginal resorption by the few Ocls that were formed (data not shown).

Effects of PPAR-γ on OPGL Signaling

Figure 5:
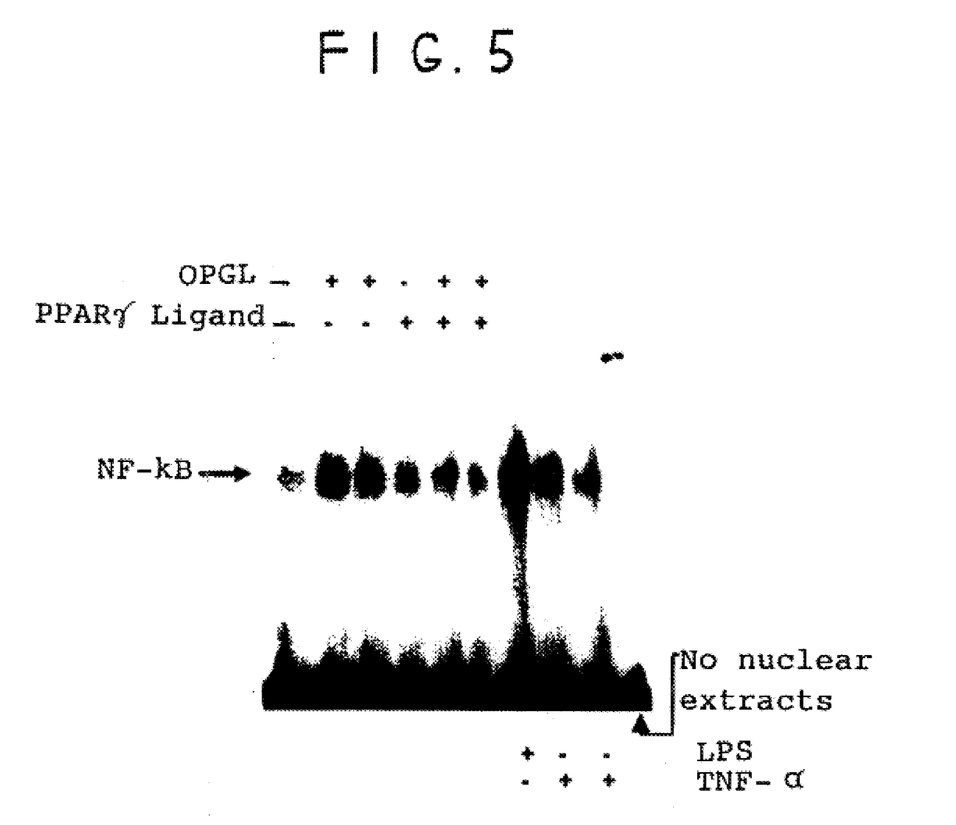
FIG. 5. Nuclear extracts from BMHCs treated with sOPGL alone for 20 min. and 40 min. (from left to right), 15d-PG-J2 alone for 30 min., or 15d-PG-J2 for 30 min. before addition of sOPGL for 20 min. and 40 min. (from left to right). Nuclear extracts from BMHCs treated with LPS or TNF-α for 30 min. (5 ng/ml and 10 ng/ml TNF-α) were used as positive controls. The data showed that the intensity of the band migrating with NF-κB induced by sOPGL was reduced markedly in the presence of 15d-PG-J2.

It has been shown previously that PPAR-γ antagonizes the NF-κB transcriptional pathway (Ricote, et al., 1998). NF-κB consists of various combinations of Rel family transcription factors, the most common being the p50/RelA dimer. First, to determine if this complex is induced by sOPGL treatment of BMMs, nuclear extracts were subjected to electrophoretic gel mobility shift assay (EMSA) in the presence or absence of anti-p50 and –RelA antibodies, using as a probe, the B3 response element of the TNF promoter. While nuclear NF-κB, in untreated BMMs, consists largely of p50 homodimers, inclusion of both antibodies, in assays containing nuclear extract of sOPGL-treated BMMs, markedly reduces the intensity of the band migrating with NF-κB. Competition with non-radiolabeled TNF-B3 and the NF-κB response element derived from the HIV1 promoter (HIV1-B), established specificity of the EMSA probe (FIG. 5). Similarly, a mutated HIV1-B (mut. HIV1-B) oligonucleotide failed to compete with TNF-B3. Secondly, to determine if PPAR-γ interferes with sOPGL-induced NF-κB activity, nuclear extracts from BMMs were treated with sOPGL and 15d-PG-J2 and subjected to EMSA. The data showed that treatment with 15d-PG-J2 markedly reduced the intensity of the band migrating with NF-κB, thereby indicating that PPAR-γ interacts with OPGL signaling through NF-κB within the osteoclast precursor.

Cited literature

Abu-Amer Y, Ross F P McHugh K P, Livolsi A, Peyron J-F, and Teitelbaum S L 1998 Tumor Necrosis Factor-Activation of Nuclear Transcription Factor-B in Marrow Macrophages Is Mediated by c-Src Tyrosine Phosphorylation of IB 273:29417

Jiang C, Ting, Seed B 1998 PPAR-γ agonists inhibit production of monocyte inflammatory cytokines. Nature 391:82–86

Kliewer S A, Lenhard J M, Willson T M, Patel I, Morris D C, Lehmann J M 1995 A prostaglandin J2 metabolite binds peroxisome proliferator-activated receptor-γ and promotes adipocyte differentiation Cell 83:813–819

Lacey D L, Timms E, Tan H-L, Kelley M J, Dunstan C R, Burgess T, Elliott R, Colombero A, Elliott G, Scully S, Hsu H, Sullivan J, Hawkins N, Davy E, Capparelli C, Eli A, Qian Y-X, Kaufman S, Sarosi I, Shalhoub V, Senaldi G, Guo J, Delaney J, Boyle WJ 1998 Osteoprotegerin ligand is a cytokine that regulates osteoclast differentiation and activation. Cell 93:165–176

Lane, et al., *J. Rheumatol*, Vol. 24, No. 6, pgs. 1132–1136 (June 1997)

Mbalaviele G, Jaiswal N, Meng A, Cheng L, van Den Bos C, Thiede M 1999 Human Mesenchymal Stem Cells Promote Human Osteoclast Differentiation From CD34+ Bone Marrow Hematopoietic Progenitors. Endocrinology, Vol. 140, pgs. 3736–3743

Ricote M, Li A C, Willson T M, Kelly C J, Glass C K 1998 The peroxisome proliferator receptor-g is a negative regulator of macrophage activation. Nature 391:79–82

Nagy L, Tontonoz P, Alvarez J G A, Chen H, Evans R M 1998 Oxidized LDL regulates macrophage gene expression through ligand activation of PPAR-γ. Cell 93:229–240

Pittenger M F, Mackay A M, Beck S C, Jaiswal R K, Douglas R, Mosca J D, Moorman M A, Simonetti D W, Craig S, Marshak D R 1999 Multilineage potential of adult human mesenchymal stem cells Science 284:143–147

Tontonoz P, Nagy L, Alvarez JGA, Thomazy VA, Evans RM 1998 PPAR-γ promotes monocyte/macrophage differentiation and uptake of oxidized LDL. Cell 93: 241–252

Xin X, Yang S, Kowalski J, Gerritsen ME 1999 peroxisome proliferator-activated receptor-γ ligand are potent inhibitors of angiogenesis in vitro and in vivo. J Biol Chem 274:9116–9121

Yasuda H, Shima N, Nakagawa N, Yamaguchi K, Kinosaki M, Mochizuki S-I, Tomoyasu A, Yano K, Goto M, Murakami A, Tsuda E, Morinaga T, Higashio K, Udagawa N, Takahashi N, Suda T 1998 Osteoclast differentiation factor is a ligand for osteoprotegerin/osteoclastogenesis-inhibitory factor. Proc Natl Acad Sci USA 95:3597–3602

Ammann P, Rizzoli R, Bonjour J P, Bourrin S, Meyer J M, Vassalli P, Garcia I 1997 Transgenic mice expressing soluble tumor necrosis factor-receptor are protected against bone loss caused by estrogen deficiency. J Clin Invest 99:1699–703

Franzoso G, Carlson L, Xing L, Poljak L, Shores E W, Brown K D, Leonardi A, Tran T, Boyce B F, Siebenlist U 1997 Requirement for NF-kappaB in osteoclast and B-cell development. Genes Dev 11:3482–96

Jaiswal N, Haynesworth S E, Caplan A l, Bruder S P 1997 Osteogenic differentiation of purified, culture-expanded human mesenchymal stem cells in vitro J Cell Biochem 64:295–312

Iotsova V, Caamano J, Loy J, Yang Y, Lewin A. Bravo R 1997 Osteopetrosis in mice lacking NF-KappaB1 and NF-kappaB2. Nat Med 3:1285–9

Kong Y-Y, Yoshida H, Sarosi I, Tan H-L, Timms E, Capparelli C, Morony S, Oliveiera-Dos-Santos A J, Van G, Itie A, Khoo W, Wakeham A, Dunstan C R, Lacey D L, Mak T W, Boyle W J, Penninger J M 1999 OPGL is a key regulator of osteoclastogenesis, lymphocyte development and lymph-node organogenesis. Nature 397:315–323

Lewis D B, Liggitt H D, Effmann E L, Motley S T, Teitelbaum S L, Jepsen K J, Goldstein S A, Bonadio J, Carpenter J, Perlmutter R M 1993 Osteoporosis induced in mice by overproduction of interleukin 4 Proc Natl Acad Sci U S A 90:11618–22

Mundy G R, Boyce B F, Yoneda T, Bonewald L F, Roodman G D 1995 Cytokines and bone remodeling. In: Marcus R, Feldman D, Kelsey J (eds) Osteoporosis. Academic Press, San Diego, Vol. 1:302–313

Poli V, Balena R, Fattori E, Markatos A, Yamamoto M, Tanaka H, Ciliberto G, Rodan G A, Costantini F 1994 Interleukin-6 deficient mice are protected from bone loss caused by estrogen depletion. EMBO J 13:1189–96

Takahashi T, Wada T, Mori M, Kokai Y, Ishii S. 1996 Overexpression of the granulocyte colony-stimulating factor gene leads to osteoporosis in mice. Lab Invest 74:827–34

Wesolowski G, Duong L T, Lakkakorpi P T, Nagy R M, Tezuka K-I, Tanaka H, Rodan G A, Rodan S B 1995 Isolation and characterization of highly enriched, prefusion mouse osteoclastic cells. Exp Cell Res 219:679–686

TABLE 1

Effects of 15d-PG-J2 on bone resorption.

|  | Ocl numbers | Pit numbers |
|---|---|---|
| Control | 108 ± 18 | 21 ± 5 |
| + 15d-PG-J2 | 107 ± 6 | 9.5 ± 0.5 |

Ocls were purified from cocultures as described in Materials and Methods then plated onto the layers of hMSCs which were seeded on elephants tusk slices. Cocultures were treated with 40 ng/ml sOPGL and 25 ng/ml M-CSF with or without 10 $\mu$M 15d-PG-J2 for 24 h. Note that treatment with 15d-PG-J2 for 24 h did not affect the numbers of Ocls but inhibited bone resorption.

What is claimed is:

1. A method for inhibiting the differentiation of CD34+ cells into osteoclasts by treating the cells with a peroxisome proliferator-activated receptor-$\gamma$ agonist.

2. The method of claim 1 wherein the CD34+ cells are hematopoietic stem cells.

3. The method of claim 1 wherein the peroxisome proliferator-activated receptor-$\gamma$ agonist is selected from the group consisting essentially of 15-deoxy-$\Delta^{12,14}$-prostaglandin-J2, ciglitazone, pioglitazone, troglitazone, and indomethacin.

4. A method for treating osteoporosis in a patient comprising administering an amount of a peroxisome proliferator-activated receptor-$\gamma$ agonist effective to reduce osteoclastogenesis.

5. A method for reducing bone resorption in a patient in need thereof comprising treating the patient with a peroxisome proliferator-activated receptor-$\gamma$ agonist in an amount effective to reduce the bone resorption.

* * * * *